(12) United States Patent
Laustsen

(10) Patent No.: US 10,316,282 B2
(45) Date of Patent: Jun. 11, 2019

(54) METHOD FOR PRODUCING A PRODUCT (E.G. POLYPEPTIDE) IN A CONTINUOUS CELL CULTURE FERMENTATION PROCESS

(71) Applicant: CMC BIOLOGICS A/S, Søborg (DK)

(72) Inventor: Mads Laustsen, Gentofte (DK)

(73) Assignee: CMC BIOLOGICS A/S, Søborg (DK)

( * ) Notice: Subject to any disclaimer, the term of this patent is extended or adjusted under 35 U.S.C. 154(b) by 406 days.

(21) Appl. No.: 14/778,222

(22) PCT Filed: Mar. 11, 2014

(86) PCT No.: PCT/EP2014/054721
§ 371 (c)(1),
(2) Date: Sep. 18, 2015

(87) PCT Pub. No.: WO2014/146933
PCT Pub. Date: Sep. 25, 2014

(65) Prior Publication Data
US 2016/0281044 A1    Sep. 29, 2016

(30) Foreign Application Priority Data

Mar. 19, 2013   (EP) ..................... 13160023

(51) Int. Cl.
| | | |
|---|---|---|
| *C12M 1/00* | (2006.01) | |
| *C12M 1/12* | (2006.01) | |
| *C12M 1/26* | (2006.01) | |
| *C12P 21/02* | (2006.01) | |

(52) U.S. Cl.
CPC ............ *C12M 23/58* (2013.01); *C12M 21/14* (2013.01); *C12M 25/02* (2013.01); *C12M 33/14* (2013.01); *C12M 47/10* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 2003/0166040 A1 | 9/2003 | Wilkins | |
| 2005/0197496 A1* | 9/2005 | Perreault | C07K 1/34 530/412 |
| 2008/0206818 A1* | 8/2008 | Wich | C07K 16/00 435/69.6 |

FOREIGN PATENT DOCUMENTS

| | | | |
|---|---|---|---|
| AU | 8217387 | * | 6/1988 |
| EP | 0062026 A2 | | 10/1982 |
| EP | 0200032 A2 | | 11/1986 |
| EP | 0270905 A2 | | 6/1988 |
| EP | 1498475 A1 | | 1/2005 |
| EP | 2014760 A1 | | 1/2009 |
| WO | 03/040380 A2 | | 5/2003 |
| WO | 2005/083052 A1 | | 9/2005 |
| WO | 2011/012725 A1 | | 2/2011 |

OTHER PUBLICATIONS

Guo, L. and Santschi, P. H. (2006) Ultrafiltration and its Applications to Sampling and Characterisation of Aquatic Colloids, in Environmental Colloids and Particles: Behaviour, Separation and Characterisation, vol. 10 (eds K. J. Wilkinson and J. R. Lead), John Wiley & Sons, Ltd, Chichester, UK. doi: 10.1002/9780470024539. ch4, 64 pages.*
Sigma Aldrich: Antibody Basics, copyright 2011, 4 pgs.*
Uniport "Cellular Component-Periplasm" 1 pg accessed at http://www.uniprot.org/locations/SL-0200 on Jan. 4, 2017.*
Medical Dictionary "Inclusion Body" 2 pages access at https://medical-dictionary.thefreedictionary.com/inclusion+body on Jan. 4, 2017.*
Matheus et al. "Liquid High Concentration IgG1 Antibody Formulations by Precipitation" Journal of Pharmaceutical Sciences, vol. 98, No. 9, Sep. 2009, pp. 3043-3057 (Year: 2009).*
Li et al. "Cell culture processes for monoclonal antibody production" MAbs. Sep.-Oct. 2010; 2(5): 466-477 (Year: 2010).*
International Search Report dated Jun. 3, 2014 from corresponding PCT/EP2014/054721; 4pgs.
Daniel Stark, et al., "In Situ Product Removal (ISPR) in Whole Cell Biotechnology During the Last Twenty Years", in Advances in Biochemical Engineering/Biotechnology, vol. 80, 2003, pp. 149-175.

* cited by examiner

*Primary Examiner* — Thane Underdahl
(74) *Attorney, Agent, or Firm* — Maier & Maier, PLLC

(57) ABSTRACT

A method for improving productivity in microbial fermentations and mammalian cell culture bioreactors.

20 Claims, 1 Drawing Sheet

B. HD chemostat

A. Prior art chemostat

C. HD chemostat with single outlet

Figure 1:
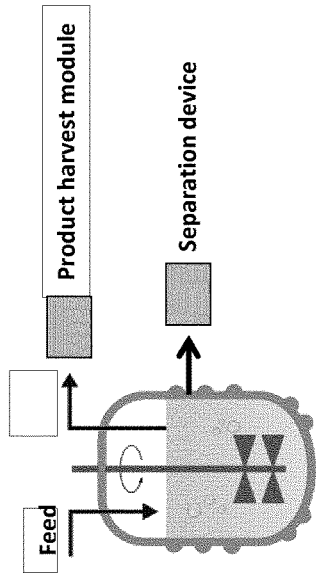
Figure 1:
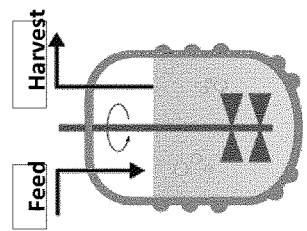
Figure 1:
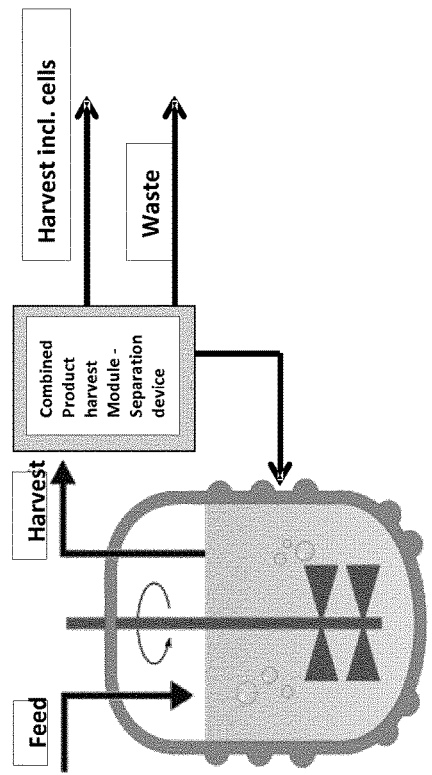

METHOD FOR PRODUCING A PRODUCT (E.G. POLYPEPTIDE) IN A CONTINUOUS CELL CULTURE FERMENTATION PROCESS

FIELD OF THE INVENTION

The present invention relates to a method for improving productivity in a continuous chemostat fermentation process.

BACKGROUND OF THE INVENTION

Traditionally, bacterial, yeast and mammalian cells are primarily cultured as suspension cultures in bioreactors, which are also, called fermenters. In such bioreactors the environmental conditions can be precisely controlled by manipulating the supply of nutrients to the cells and the removal of waste materials and a stirring means may move the culture medium in the interior of the reactor providing for a homogeneous distribution of the cells.

The bioreactor may be operated as a closed system such as a batch or fed-batch system or as a continuous system, such as a perfusion system or a chemostat system.

In a batch operation, the reactor is operated discontinuously. At the beginning of a batch, the culture medium usually contains a medium with the necessary nutrients, for example glucose, vitamins, amino acids and minerals. During fermentation, these are consumed so that the medium becomes more and more deprived in nutrients. At the same time, the concentration of waste products increases which finally results in a prevention of the cell growth. The viable cell density achieves a maximum value and thereafter decreases again. Consequently, the culturing is normally discontinued when the maximum cell density is reached or minimum cell viability is reached. The content of the reactor is then passed on for further downstream processing.

In this regard the so-called "feedbatch (alternatively named fed-batch) process" is a process in which, during the fermentation procedure, fresh culture medium is supplied (fed) to the bioreactor in order to supply more nutrients as those there are consumed during the bioreactor process. However, in practice this process has limitations to the volume that can be added and it does not provide for removal of waste products that might be harming the cell growth and productivity. Thus a feedbatch process does not provide any substantial advantages due to an increase of the waste materials.

The bioreactor may also be operated as a continuous system such as in a perfusion system or a chemostat system. In a perfusion system, the waste/impurities in the medium is continuously removed from the culture and the displaced medium is replenished with fresh medium. The constant addition of fresh medium and elimination of waste products provides the cells with the environment they require to achieve high cell concentrations and with that a higher productivity. Thus, it is possible to achieve a state of equilibrium in which cell concentration and productivity are maintained. Product may be continuously harvested by taking out medium (with cells and product).

A chemostat system is operated with a continuous inflow of medium and an outflow of cells and products keeping the culture volume constant. One of the most important features of chemostat systems is that microorganisms can be grown in a physiological steady state. In steady state, growth occurs at a constant rate and all culture parameters remain constant. Normally, in chemostat systems, there is no cell retention device, such that the concentration of cells in the bioreactor and the concentration of the cells in supernatant harvested from the bioreactor are substantially identical. Typically, culture medium is fed to the reactor at a predetermined and constant rate, maintaining a low dilution rate of the culture. To prevent washout of cells, the dilution rate generally is chosen to be less than, and sometimes equal to, the maximum specific growth rate of the cells. Culture fluids containing cells, cell products, by-products, waste products, etc., are removed through one common outlet at the same rate, or substantially the same rate. Compared to the perfusion system, the chemostat system typically results in lower cell densities and an inherent disadvantage of the chemostat systems is that the feed of the nutrients cannot be controlled independent of the product and/or cell harvest flow leading to a low productivity and high manufacturing cost of goods.

WO2011012725 describes a continuous cell culture strategy for producing polypeptides or viruses of interest in mammalian, cell culture wherein the cell culture system comprises a cell retention device consisting of a macroporous microcarrier such that the culture can be sustained for a prolonged period of time. However, WO2011012725 does not describe a method for producing a product in a chemostat fermentation process, wherein the bioreactor comprises one outlet having a separation device allowing impurities with a size below the size of the product, and medium to be removed and another independent outlet for removal of product, cells, cell products, by-products, waste products, etc.

In FIG. 1A herein is shown a typical prior art reactor having one inlet for adding medium and one outlet for harvesting the product of interest together with the culture fluids containing cells, cell products, by-products, waste products, etc. In other words, the continuous cell culture strategy described in e.g. WO2011012725 lacks the possibility to remove by-products, waste products and impurities through one outlet and harvest the product of interest through a second outlet.

SUMMARY OF THE INVENTION

The problem to be solved by the present invention is to provide a continuous chemostat fermentation process for improving cell densities and thereby increasing productivity of a bioreactor and the concentration of the product in the harvested medium, where productivity of a product (e.g. a polypeptide) can be improved due to e.g. optimized conditions for cell growth.

The solution is based on that the present inventor has found that by having a first outlet on a bioreactor equipped with a separation device (e.g. a impurity filter unit) allowing impurities with a size below the size of the product, and medium to be removed with one flow rate and a second outlet for harvesting the product of interest together with the culture fluid containing cells, cell products, by-products and waste products using the same or a different flow rate, one can obtain an increased cell density in the reactor during the fermentation process and in particular one can get a significant higher concentration of the product of interest in the harvested medium as well as an increased productivity per liter spend medium.

As illustrated in FIGS. 1B and C herein, the solution of the present invention, wherein the bioreactor comprises a separation device to allow impurities to be removed by one outlet while cells and/or product is removed by another independent outlet permit separating the feed into a waste fraction that is passing through a separation device and a harvest fraction that is passing through a product harvest module. The skilled person knows a number of suitable a separation devices e.g. membrane filters (see below for further details).

By separating the outflow into a harvest fraction containing product and/or cells and a waste fraction containing impurities and spend media, a higher concentration of high value media components such as e.g. growth factors may be achieved inside the bioreactor for a prolonged time while still keeping the level of impurities low. Moreover, the flow of product and/or cells leaving the bioreactor may also be controlled by adjusting the flow rate through the product harvest module and a significant higher concentration of the product of interest and an increased productivity per liter spend medium may be obtained.

This is illustrated in working examples 1 and 2 herein. In working example 1, no separation device is operating and all the feed solution is directed out through the product harvest outlet. In working example 2, the bioreactor has one outlet equipped with a separation device allowing impurities with a size below the size of the product, and medium to be removed and a second outlet for harvesting the product i.e. antibody. The bioreactor is feed with 7.5 L/day where 5 L/day is directed out through the impurity filter unit and 2.5 L/day is directed out through the harvesting outlet. This gives a significant improvement compared to example 1, and the productivity is increased by a factor of 3 (0.69 g/L day compared to 0.22 g/L day), and the harvest concentration with a factor of 5 (1.38 g/L compared to 0.27 g/L). It is remarkable that this is achieved while at the same time the media consumption per gram of product is being significantly reduced.

Accordingly, a first aspect of the present invention relates to a method for producing a product selected from a biopolymer expressed by a cell, an intracellular or extracellular product produced by a cell or microorganism, a periplasmatic product produced by a cell or microorganism, a cell, or a microorganism in a bioreactor in a chemostat fermentation process, wherein said bioreactor comprises:

i) a first outlet having a separation device allowing impurities with a size below the size of the product, and medium to be removed while retaining the product in the bioreactor;

(ii) a second outlet having a product harvest module allowing the product, cells, impurities and medium to be removed; and (iii) an inlet for adding a medium;

wherein the method comprises the following steps:

(a) fermenting the cell expressing the biopolymer, the cell or microorganism producing the intracellular product, the cell or microorganism producing the periplasmatic product, the cell, or the microorganism in the bioreactor in a suitable medium under suitable conditions, wherein during the fermentation impurities and medium are removed via the separation device, the product, cells, impurities and medium are removed via the product harvest module and new medium is added to replenish nutrients consumed by the cells or microorganisms and to equilibrate the medium removed during removal of impurities and harvesting the product; and (b) the product is isolated from the harvested medium; and wherein the cell density in the bioreactor during the fermentation reaches at least 5 million cells per ml medium.

A second aspect of the present invention relates to a method for producing a harvest comprising a product selected from a biopolymer expressed by a cell, an intracellular product, such as an inclusion body, produced by a cell or microorganism, a periplasmatic product, such as a precipitated product in solid form, produced by a cell or microorganism, a cell or a microorganism in a bioreactor in a chemostat fermentation process, wherein said bioreactor comprises:

i) a first outlet having a separation device (e.g. an impurity filter unit) allowing impurities with a size, such as molecular weight (MW) below the size (e.g. MW) of the product, and medium to be removed while retaining the product in the bioreactor;

(ii) a second outlet having a product harvest module allowing the product, cells, impurities and medium to be removed; and (iii) an inlet for adding a medium;

wherein the method comprises the following step:

fermenting the cell expressing the biopolymer, the cell or microorganism producing the intracellular product, such as inclusion bodies, the cell or microorganism expressing the periplasmatic product, the cell or the microorganism in the bioreactor in a suitable medium under suitable conditions, wherein during the fermentation impurities and medium are removed via the separation device, the product, cells, impurities and medium are removed via the product harvest module and new medium is added to replenish nutrients consumed by the cells or microorganisms and to equilibrate the medium removed during removal of impurities and harvesting the product; and wherein the cell density in the bioreactor during the fermentation reaches at least 5 million cells per ml medium.

A third aspect of the present invention relates to a high density chemostat apparatus comprising a bioreactor for fermenting a cell expressing the biopolymer, a cell or microorganism producing an intracellular product, such as inclusion bodies, a cell or microorganism expressing a periplasmatic product, a cell or a microorganism having:

i) a first outlet having a separation device allowing impurities with a size below the size of the product to be removed while retaining the product in the bioreactor;

(ii) a second outlet having a product harvest module allowing the product, cells, impurities and medium to be removed;

(iii) a first inlet for adding a medium.

In some cases if the polypeptide of interest has limited stability or exhibit toxic effects on the host cell it may be convenient to express it under control of an inducible promoter such that the cells first are grown to a desired cell density and then the expression of the polypeptide is induced by adding an inducer or by changing the temperature and or the pH of medium.

Accordingly, a fourth aspect of the present invention relates to a method for producing a product selected from a biopolymer expressed by a cell, an intracellular or extracellular product produced by a cell or microorganism, a periplasmatic product produced by a cell or microorganism, in a first and a second bioreactor in a chemostat fermentation process, wherein said first bioreactor comprises:

i) optionally a first outlet having a separation device allowing impurities with a size below the size of the product, and medium to be removed while retaining the product in the bioreactor;

(ii) a second outlet having a product harvest module allowing the product, impurities and medium to be removed; and (iii) an inlet for adding a medium;

wherein said second bioreactor comprises:

(iv) a third outlet having a separation device allowing impurities with a size below the size of the product, and medium to be removed while retaining the product in the bioreactor;

(v) a fourth outlet having a product harvest module allowing the product, impurities and medium to be removed; and (vi) an inlet for adding a medium;

(vii) an inlet for adding cells and a medium from the first bioreactor;

wherein the first bioreactor is for growth of cells or microorganisms and the second bioreactor is for induction of production of the biopolymer, the intracellular or extracellular product, or the periplasmatic product, and wherein the first and second bioreactor operates in series, wherein the method comprises the following steps:

(a) growing and optionally fermenting the cell expressing the biopolymer, the cell or microorganism producing the intracellular or extracellular product, the cell or microorganism producing the periplasmatic product, the cell, or the microorganism in the first bioreactor in a suitable medium under suitable conditions, wherein during the growing and optionally fermentation impurities and medium are removed via the separation device, the product, cells, impurities and medium are removed via the product harvest module and new medium is added to replenish nutrients consumed by the cells or microorganisms and to equilibrate the medium removed during removal of impurities and harvesting the product; and (b) transporting the product, impurities and medium removed via the product harvest module to the second bioreactor, induction of production of the biopolymer, the intracellular or extracellular product, or the periplasmatic product, wherein during the production impurities and medium are removed via the separation device, the product, cells, impurities and medium are removed via the product harvest module and new medium is added to replenish nutrients consumed by the cells or microorganisms and to equilibrate the medium removed during removal of impurities and harvesting the product (c) the product is isolated from the harvested medium; and wherein the cell density in the bioreactor during the fermentation reaches at least 5 million cells per ml medium.

DEFINITIONS

Prior to a discussion of the detailed embodiments of the invention is provided a definition of specific terms related to the main aspects and embodiments of the invention. All terms are defined in accordance with the skilled person's normal understanding of the terms.

As used herein the term "a chemostat fermentation process" is intended to mean a fermentation process taking place in a bioreactor in a chemostat system. The chemostat system for fermentation processes are operated with a continuous inflow of medium comprising nutrients and an outflow of culture medium comprising cells, products, waste products, used media etc. In the chemostat system, there is no cell retention device, such that the concentration of cells in the bioreactor and the concentration of the cells in supernatant harvested from the bioreactor are substantially identical. Typically, culture medium is fed to the reactor at a predetermined and constant rate, maintaining a low dilution rate of the culture (typically 0.2 $d^{-1}$ to 1.0 $d^{-1}$). To prevent washout of cells, the dilution rate generally is chosen to be less than, and sometimes equal to, the maximum specific growth rate of the cells. Culture fluids containing cells, cell products, by-products, waste products, etc., are removed at the same rate, or substantially the same rate. Chemostat systems typically provide for a high degree of control, since the cultures may equilibrate, i.e., reach a steady state at a specific growth rate equivalent to the dilution rate. This equilibration is determinative of the concentration of the cells, metabolites, waste products, expressed products (e.g. secreted proteins), etc. Specific growth rates in chemostat systems are typically lower than the maximum growth rate due to at least one limiting substrate. In some systems, however, steady states may be maintained at the maximum specific growth rates by controlling and adjusting biomass, e.g., in turbidstat systems of chemostat cultures. Typically, such chemostat cultures contain a homogeneous distribution of cells (e.g., single cell suspensions) throughout the bioreactor. Compared to the perfusion system, however, the chemostat system typically results in lower cell densities.

As used herein the term "a chemostat apparatus" is intended to mean an apparatus comprising a bioreactor for operating in a chemostatic mode. Thus, in the chemostat fermentation process a chemostat apparatus is used for hosting and fermenting the cells and microorganisms in a medium.

As used herein the term "bioreactor" refers to any device or system that supports a biologically active environment. In one case but not limited to, a bioreactor is a vessel in which is carried out a chemical process which involves organisms or biochemically active substances derived from such organisms. This process can either be aerobic or anaerobic. Bioreactors are commonly cylindrical, ranging in size from some liters to cubic meters, and are often made of stainless steel but could also be made of other materials such as disposable materials.

A bioreactor may also refer to a device or system meant to grow cells or tissues in the context of cell culture. On the basis of mode of operation, a bioreactor may be classified as batch, fed-batch or continuous (e.g. continuous stirred-tank reactor model). An example of a bioreactor is the chemostat. The bioreactor may be equipped with one or more inlets for supplying new fresh or concentrated medium to the cells, and with one or more outlets for harvesting product or emptying the bioreactor. Additionally, the bioreactor may be equipped with at least one outlet constructed in such a way that a separation device can be attached to the bioreactor. Typically the bioreactor's environmental conditions like gas (i.e., air, oxygen, nitrogen, carbon dioxide) flow rates, temperature, pH and dissolved oxygen levels, and agitation speed/circulation rate can be closely monitored and controlled.

As used herein the terms "a first outlet" and "a second outlet" is intended to mean "one or more first outlets" and "one or more second outlets", and such first and second outlets may be different and individual outlets directly fitted to the bioreactor, or the first and second outlets may be in communication with the bioreactor through a single outlet directly fitted to the bioreactor, wherein the separation takes place outside the bioreactor. The same applies to the terms "a third outlet" and "a fourth outlet" in connection with the additional bioreactor system.

Embodiments of the present invention are described below, by way of examples only.

DRAWINGS

FIG. 1: This figure shows a typical prior art chemostat bioreactor and examples of novel chemostat bioreactors as described herein. FIG. 1A shows a normal prior art chemostat bioreactor where all the feed passes through the product harvest module. FIG. 1B shows a novel chemostat bioreactor having one outlet equipped with a separation device for removing impurities and a second outlet for harvesting the product. FIG. 1C shows a variant of the chemostat bioreactor of FIG. 1 B where the separation device and the product harvest module are build into one common unit fitted onto one outlet and where the effluent is split into the separation device and the product harvest module outside the bioreactor and the retentate is lead back to the bioreactor.

DETAILED DESCRIPTION OF THE INVENTION

The present inventor has found that by having one outlet on a bioreactor equipped with a separation device (e.g. a impurity filter unit) allowing impurities with a size below the size of the product, and medium to be removed with one flow rate and another outlet for harvesting the product of interest together with the culture fluid containing cells, cell products, by-products and waste products with the same or a different flow rate, one can get an increased cell density in the bioreactor during a chemostat process and in particular one can get a significant higher concentration of product of interest in the harvested medium and as well as an increased productivity per liter spend medium. This chemostat process may also be called herein a high-density chemostat or just HD chemostat.

The product of interest may be a biopolymer expressed by a cell, an intracellular or extracellular product produced by a cell or microorganism, a periplasmatic product produced by a cell or microorganism, a cell or a microorganism.

As used herein biopolymers are a special class of polymers produced by living organisms. Biopolymers are made of repetitive units called monomers. Biopolymers inherently have a well-defined structure: The exact chemical composition and the sequence in which these units are arranged is called the primary structure. Many biopolymers spontaneously fold into characteristic compact shapes, which determine their biological functions. Starch, proteins and peptides, DNA, and RNA are all examples of biopolymers, in which the monomer units, respectively, are sugars, amino acids, and nucleic acids.

In a suitable example the biopolymer of interest has a MW of at least 2,000 kDa, or at least 5,000 kDa, or at least 15,000 kDa, or at least 25,000 kDa, or at least 50,000 kDa, or at least 100,000 kDa, or at least 150,000 kDa, or at least 200,000 kDa, or at least 250,000 kDa.

Suitable examples of a biopolymer of interest include a polypeptide, polysaccharide, polypeptide/polysaccharide hybrid, polynucleotide, which are polymers derived from ribonucleic acid (RNA) and deoxyribonucleic acid (DNA), polyhydroxybutyrate a class of polyesters produced by certain bacteria, cis-1,4-polyisoprene the major component of rubber tree latex.

However, in a suitable example the polypeptide of interest has a MW of at least 5,000 kDa, or at least 15,000 kDa, or at least 20,000 kDa or at least 40,000 kDa or at least 50,000 kDa, or at least 100,000 kDa, or at least 150,000 kDa, or at least 200,000 kDa, or at least 250,000 kDa, or at least 500,000 kDa.

In a preferred embodiment of the present invention the product is selected from a biopolymer, such as a polypeptide or protein.

Suitable examples of a polypeptide of interest include an antibody or fragment thereof, Human growth hormone, Follicle-stimulating hormone, Factor VIII, Factor VII, Factor IX Erythropoietin (EPO), Granulocyte colony-stimulating factor (G-CSF), alpha-glactosidase A, alpha-L-iduronidase (rhIDU; laronidase), N-acetylgalactosamine-4-sulfatase (rhASB; galsulfase), DNAse, Tissue plasminogen activator (TPA), Glucocerebrosidase, Interferon (IF), Insulin, Insulin derivative, Insulin-like growth factor 1, Tenecteplase, antihemophilic factor, human coagulation factor, Etanercept, Trastuzumab, Infliximab, Basiliximab, Belimumab, Daclizumab, Adalimumab Abciximabor, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

In a preferred embodiment of the present invention the product is insulin, such as human insulin.

Cells expressing a polypeptide may do this either under control of a constitutive promoter (i.e. an unregulated promoter that allows for continual transcription of its associated gene) or under control of an inducible promoter (promoters induced by the presence or absence of biotic or abiotic factors). In some cases if the polypeptide of interest has limited stability or exhibit toxic effects on the host cell it may be convenient to express it under control of an inducible promoter such that the cells first are grown to a desired cell density and then the expression of the polypeptide is induced by adding an inducer or by changing the temperature and or the pH of medium.

As used herein "induction of production of the biopolymer, the intracellular or extracellular product, or the periplasmatic product" refers to changing the state of the bioreactor such that the cells increase production of the biopolymer, the intracellular or extracellular product, or the periplasmatic product compared to the state before induction of production of the biopolymer, the intracellular or extracellular product, or the periplasmatic product. This may be initiated by adding a chemical compound e.g. an inducer to the medium, by changing the temperature and/or the pH of the medium or by leading more or less oxygen through the bioreactor.

In one embodiment of the present invention, induction of production of the biopolymer, the intracellular or extracellular product, or the periplasmatic product, is initiated by changing the temperature, and/or the pH of the medium or by adding a chemical compound such as an inducer.

The skilled person knows how to select suitable constitutive promoter depending on the host cell. Some well known mammalian constitutive promoters are the Simian virus 40 early promoter (SV40), cytomegalovirus immediate-early promoter (CMV), human Ubiquitin C promoter (UBC), human elongation factor 1α promoter (EF1A), mouse phosphoglycerate kinase 1 promoter (PGK), and chicken β-Actin promoter coupled with CMV early enhancer (CAGG) copia transposon promoter (COPIA), actin 5C promoter (ACT5C) and Chinese hamster elongation factor-1 alpha promoter (CHEF1).

Inducible promoters are a very powerful tool in genetic engineering because the expression of genes operably linked to them can be turned on or off at certain stages. The skilled person knows how to select suitable constitutive promoter depending on the host cell and the type of inducer. Inducible promoters may either be regulated by biotic or abiotic factors. Examples of inducible promoter regulated by abiotic factors such as heat is the heat shock transcription factor 1 (HSF1) and examples of inducible promoter regulated by biotic factors (e.g. chemical inducers) are the T-REx™ System; a tetracycline-regulated mammalian expression system that uses regulatory elements from the *E. coli* Tn10-encoded tetracycline (Tet) resistance operon, the Ecdysone-Inducible Expression System that can be induced by a steroid hormone.

The isolated biopolymer (e.g. polypeptide) of interest is normally purified and formulated into a final commercial relevant composition of interest (e.g. a pharmaceutical composition of interest). Further it is normally packaged in a suitable container. Thus, in one embodiment the isolated polypeptide is formulated into a pharmaceutical composition.

An intracellular product may in general be any intracellular localized compound such as an organelle enclosed within its own lipid bilayer, such as an inclusion body, a virus or a biopolymer as described above, a vitamin, a fatty acid, an alcohol or any other low molecular organic compound produced by a cell.

In a preferred embodiment of the present invention the intracellular product is an inclusion body.

An extracellular product may in general be any compound that has been produced or synthesized by a cell and actively or passively exported out from the cell. Examples of extracellular product may be biopolymers, hormones, growth factors, enzymes, proteinases, cytokines chemokines or other compounds that are transported out from the cell. In general it is easier to purify an extracellular product than an intracellular localized product since it is not necessary to disrupt the cell wall and isolate the product from the complex disrupted cellular composition.

The product may also be a periplasmatic product produced by a cell or microorganism. As used herein, the periplasm is a space bordered by two selective permeable barriers, i.e. biological membranes, which are the inner membrane (i.e. cytoplasmic membrane) and the outer membrane in Gram-negative bacteria. Products of interest may be naturally localized to the periplasm or genetically equipped with relevant signal peptides for active transportation to periplasm. Purification of proteins from the periplasm extract is relatively easy because the level of impure proteins is lower than that in intracellular expression methods.

In one embodiment the product is selected from a periplasmatic product, such as a precipitated product in solid form and in a further embodiment the periplasmatic product is a precipitated product in solid form, such as in crystalline, amorphous or denatured form.

As used herein the product may also be a cell. The cell is the basic structural and functional unit of all known living organisms. There are two types of cells: eukaryotic and prokaryotic. Prokaryotic cells are usually independent, while eukaryotic cells can either exist as a single celled organism or be found in multicellular organisms. The prokaryote cell is simpler, and therefore smaller, than a eukaryote cell, lacking a nucleus and most of the other organelles of eukaryotes. There are two kinds of prokaryotes: bacteria and archaea; these share a similar structure. Plants, animals, fungi, slime moulds, protozoa, and algae are all eukaryotic. The major difference between prokaryotes and eukaryotes is that eukaryotic cells contain membrane-bound compartments in which specific metabolic activities take place. Most important among these is a cell nucleus, a membrane-delineated compartment that houses the eukaryotic cell's DNA.

In one embodiment the product is selected from a cell, such as a mammalian cell.

In a further embodiment the cell expressing the polypeptide is at least one cell selected from the group consisting of *E. coli, Bacillus*, yeast from the genus of *Saccharomyces, Pichia, Aspergillus, Fusarium, Kluyveromyces*, CHO (Chinese Hamster Ovary) cell, hybridomas, BHK (Baby Hamster Kidney) cell, myeloma cell, HEK-293 cell, human lymphoblastoid cell, a human cell such as PER.C6® human cell and a mouse cell.

In a still further embodiment the cell is selected from a mammalian cell line such as CHO, NSO, Perc6, BHK, or HEK. In a preferred embodiment the cell is a mammalian cell.

As used herein a microorganism include all of the prokaryotes, namely the bacteria and archaea; and various forms of eukaryote, comprising the protozoa, fungi, algae, microscopic plants (green algae), and animals such as rotifers planarians and also virus. In one embodiment of the invention the microorganism is selected from fungus, yeast, *humicola, saccharomyces, aspergillus, bacillus, lactobacillus*.

As used herein the product may be an intracellular product such as a virus. A virus is a small infectious agent that only replicate inside the living cells of an organism. Viruses can infect all types of organisms, from animals and plants to bacteria and archaea. Viral populations do not grow through cell division, because they are a-cellular. Instead, they use the machinery and metabolism of a host cell to produce multiple copies of themselves, and they assemble inside the cell. Vaccination may be an effective way of preventing infections by viruses. Vaccines can consist of live-attenuated or killed viruses, or viral proteins (antigens). Live vaccines contain weakened forms of the virus, which do not cause the disease but, nonetheless, confer immunity. Such viruses are called attenuated. Biotechnology and genetic engineering techniques are used to produce subunit vaccines. These vaccines use only the capsid proteins of the virus. Hepatitis B vaccine is an example of this type of vaccine. In an embodiment of the present invention the product is a virus or a part of a virus.

In a preferred embodiment the product is selected from a microorganism, such as yeast, virus and bacteria.

As used herein a bioreactor is any device or system that supports a biologically active environment. In one case but not limited to, a bioreactor is a vessel in which is carried out a chemical process which involves organisms or biochemically active substances derived from such organisms. This process can either be aerobic or anaerobic. Bioreactors are commonly cylindrical, ranging in size from some liters to cubic meters, and are often made of stainless steel but could also be made of other materials such as disposable materials. The bioreactor may be a so-called single-use bioreactor or disposable bioreactor. Disposable bioreactors are well known in the art. Instead of a culture vessel made from stainless steel or glass, a single-use bioreactor is equipped with a disposable bag. The disposable bag may be made of a three-layer plastic foil. One layer is made from Polyethylene terephthalate or LDPE to provide mechanical stability. A second layer made using PVA or PVC acts as a gas barrier. Finally, a contact layer is made from PVA or PP. In general there are two different approaches for constructing single-use bioreactors, differing in the means used to agitate the culture medium.

Some single-use bioreactors use stirrers like conventional bioreactors, but with stirrers that are integrated into the plastic bag. The closed bag and the stirrer are pre-sterilized. In use the bag is mounted in the bioreactor and the stirrer is connected to a driver mechanically or magnetically. Other single-use bioreactors are agitated by a rocking motion. This type of bioreactor does not need any mechanical agitators inside the single-use bag. Both the stirred and the rocking motion single-use bioreactors are used up to a scale of 2000 to 5000 liters volume. Compared with conventional bioreactor systems, the single-use solution has some advantages. Application of single-use technologies reduces cleaning and sterilization demands. Some estimates show cost savings of more than 60% with single use systems compared to fixed asset stainless steel bioreactors. In pharmaceutical production, complex qualification and validation procedures can be made easier, and will finally lead to significant cost reductions. The application of single-use bioreactors reduces the risk of cross contamination and enhances the biological and process safety. Single-use applications are especially suitable for any kind of biopharmaceutical product. Moreover, single-use bioreactors contain fewer parts compared with conventional bioreactors, so the initial and maintenance costs are reduced. In one embodiment of the present invention the bioreactor is a single-use bioreactor such as a disposable bioreactor.

A bioreactor may also refer to a device or system meant to grow cells or tissues in the context of cell culture. On the basis of mode of operation, a bioreactor may be classified as batch, fed-batch or continuous (e.g. continuous stirred-tank reactor model). An example of a bioreactor is the chemostat. The bioreactor may be equipped with one or more inlets for supplying new fresh or concentrated medium to the cells and one or more outlets for harvesting product or emptying the bioreactor constructed in such a way that a separation device can be attached to the bioreactor.

In a preferred embodiment the bioreactor has a volume of at least 50 L, more preferably at least 100 L, even more preferably at least 250 L and most preferably at least 500 L.

As used herein a separation device may be an impurity filter unit, such as a membrane filter or a gravitational separation unit or a centrifugal separation unit.

Several specialized filters and filtration methods have been developed to separate materials according to their chemical and physical properties. Filters, which have been developed in the art, include flat surface filters, pleated filters, multi-unit cassettes, and tubular forms such as hollow fibers. For the invention described herein any system of ultrafiltration technology can be applied as long as sterility can be ensured. Examples of filtration systems applicable for use in the production of polypeptides and removal of impurities as described herein are systems like: cartridge systems, plate and frame and hollow fiber systems. The systems can be operated by pumping of liquid over the membrane, by vibration (like supplied by PallSep) or by alternating tangential flow (ATF) and both polymeric and ceramic membranes are well suited for the filtration process. A skilled person knows to select a membrane with the right properties.

Hollow fiber membranes have been successfully employed in a wide variety of industries including food, juice, pharmaceutical, metalworking, dairy, wine and most recently municipal drinking water. Depending on the application, hollow fiber membranes can be highly practical and cost effective alternatives to conventional chemical and physical separation processes. Hollow fiber membranes offer the unique benefits of high membrane packing densities, sanitary designs and, due to their structural integrity and construction, can withstand permeate back-pressure thus allowing flexibility in system design and operation. Hollow fiber cartridges can operate from the inside to the outside during filtration. This means that process fluid (retentate) flows through the centre of the hollow fiber and permeate passes through the fiber wall to the outside of the membrane fiber. Tangential flow can help limit membrane fouling. Other operating techniques that can be employed with hollow fiber membrane systems include back flushing with permeate and retentate reverse flow.

Accordingly the filter may be located in an external filter module attached to the bioreactor. Alternatively the impurity filter may be located inside the bioreactor. The filter unit can also contain pumps or systems for preventing fouling of the filter such as the ATF system described above or the Pallsep system where, controlled horizontal oscillation moves the membrane elements through the feed fluid. The oscillation generates vibrational energy at the membrane surface, giving shear (higher than that typically generated in conventional Tangential Flow Filtration systems) that is limited to a small boundary layer above the membrane surface, and which is not applied to the bulk of the fluid. This ensures that even in high solids feed streams, the membranes do not cake with the retained species. Fluids are processed in a very gentle manner through an open flow path with minimal pressure drop and even transmembrane pressure distribution.

The system can dependent on the metabolites needed to be removed from the process and the product in question be equipped with membranes with a molecular cut off value from few hundreds to tens of thousand. Often membranes with a cut off between 1,000 and 20,000 are used. The benefit of using a membrane with a cut off of 10,000 or below preferably around 5,000 being that growth factors like Insulin and IGF-1 will be retained in the bioreactor.

Moreover, during an extended run, a filter may be changed and the system resterilized without terminating the fermentation.

The skilled person knows what could be a suitable filter type for removal of impurities and a suitable membrane nominal molecular weight cut-off (NMWC) pore sizes with respect to allowing impurities to perfuse out of the impurity filter and harvest the polypeptide of interest through the product harvesting outlet.

In one embodiment the separation device is selected from an impurity filter unit, such as a membrane filter or a gravitational separation unit or a centrifugal separation unit.

The impurity filter is often selected within the range of 1000 to 30,000 NMWC, such as e.g. in the range of 2000 to 20,000 NMWC or in the range of 2000 to 15,000 NMWC. However, if the product is a cell the impurity filter may be selected within the range of 1000 to 500,000 NMWC, but normally it is preferred that the impurity filter has a cut-off of less than 20,000 NMWC. Thus, in one embodiment the impurity filter unit is a membrane filter having a nominal molecular weight cut-off (NMWC) pore sizes of at least 1000 NMWC, such as within the range of 2000 to 15,000 NMWC.

In a preferred embodiment the impurity filter unit is a membrane filter having a molecular weight cut-off (NMWC) pore size of a maximum of 80% of the MW of the product (e.g. polypeptide) of interest. For instance, if MW of polypeptide of interest is 100,000 the preferred maximum cut-off of the impurity filter is 80,000 NMWC. Even more preferably, the impurity filter has a molecular weight cut-off (NMWC) pore size of a maximum of 50% of the MW of the polypeptide of interest. Thus, in one embodiment the impurity filter has a molecular weight cut-off (NMWC) pore size of a maximum of 80% of the MW of the biopolymer.

It may be an advantage that the NMWC of the impurity filter is relatively low if the media comprises useful compounds such as e.g. insulin, which has a MW of around 6 kDa. Accordingly, if e.g. insulin is present in the medium the NMWC of the impurity filter is preferably 10,000 or below.

As used herein a product harvest module is in its most simple form just an outlet leading to a container or bag suitable for collecting the product with cells, impurities and medium for storage or further downstream processing. It may also be a separation device capable of for example separating polypeptides from cells, cell debris or impurities lager than the product of interest.

Overall there are two major classes of techniques for the separation of cells from the medium in chemostat bioreactors, namely, by gravitational or centrifugal sedimentation, and by filtration (e.g. tangential filtration such as axial rotation filtration or as spin filters or cross flow filtration).

A gravitational separation is an industrial method of separating two components, either a suspension, or dry granular mixture where separating the components with gravity is practical. This method can be used to separate out solids from a liquid mixture, if the solids are not soluble in the liquid. The skilled person knows to attach suitable gravitational separation devises to a bioreactor.

Centrifugal separation is another well-known technique to separate out particles in suspension. Commercially available separators utilizing centrifugal force for separation fall in one of two categories, rotary centrifuges or hydrocyclones. In centrifuges, the centrifugal force is mechanically generated by turning the equipment containing the fluid in a circular path causing the fluids to separate. It has mainly been used to separate fluids in static state, i.e., specific volumes, which needed to be separated. Hydrocyclones are operated by creating a physical vortex within a cylindrical vessel generating centrifugal force. The heavier phase is forced to the outside portion of the fluid and the lighter fluid stays in the inside as a core. As the fluid continues flowing, the separated portions are directed to different outlets. The skilled person knows to attach suitable centrifugal separation devises to a bioreactor.

In an embodiment the product harvest module is a separation device based on gravitational or centrifugal sedimentation.

In a further embodiment the product harvest module is a filter unit. In such a case the product harvest module may herein be termed product filter.

In certain cases the separation device and the product harvest module may be build into one common unit fitted onto one outlet. In such a system the effluent is split into the separation device and the product harvest module outside the bioreactor and the retentate is lead back to the bioreactor.

Thus, in one embodiment the separation device and the product harvest module is build into one common unit fitted onto a single outlet. In another embodiment the separation device and the product harvest module are different and have individual outlets fitted to the bioreactor.

In a preferred embodiment outlet having a separation device allowing impurities with a size below the size of the product, and medium to be removed while retaining the product in the bioreactor and the outlet having a product harvest module allowing the product, cells, impurities and medium to be removed are different and independent.

As used herein "medium" generally refers to, a cell culture medium, which may comprises salts, amino acids, vitamins, lipids, detergents, buffers, growth factors, hormones, cytokines, trace elements and carbohydrates. Examples of salts include magnesium salts, for example $MgCl_2 \times 6H_2O$ and iron salts, for example $FeSO_4 \times 7H_2O$, potassium salts, for example $KH_2PO_4$, KCl; sodium salts, for example $NaH_2PO_4$ or $Na_2HPO_4$ and calcium salts, for example $CaCl_2 \times 2H_2O$. Examples of amino acids are all 20 known proteinogenic amino acids, for example histidine, glutamine, threonine, serine, methionine. Examples of vitamins include: ascorbate, biotin, choline, myo-inositol, and D-panthothenate, riboflavin. Examples of lipids include: fatty acids, for example linoleic acid and oleic acid; soy peptone and ethanol amine. Examples of detergents include Tween 80 and Pluronic F68. An example of a buffer is HEPES. Examples of growth factors/hormones/cytokines include IGF, hydrocortisone and (recombinant) insulin. Examples of trace elements are known to the person skilled in the art and include Zn, Mg and Se. Examples of carbohydrates include glucose, fructose, galactose and pyruvate. However, for manufacturing industrial low cost products the medium could also include low cost complex components like starch and protein sources from food stock, etc. The skilled person knows what could be suitable medium and suitable conditions with respect to specific expression cells and polypeptide of interest.

The pH, temperature, dissolved oxygen concentration and osmolarity of the cell culture medium depend on the type of cell chosen. Preferably, the pH, temperature, dissolved oxygen concentration and osmolarity are chosen such that it is optimal for the growth and productivity of the cells. The person skilled in the art knows how to find the optimal pH, temperature, dissolved oxygen concentration and osmolarity for the chemostat culturing. Usually, the optimal pH for mammalian cells is between 6.6 and 7.6, the optimal temperature between 30 and 39 C, the optimal osmolarity between 260 and 400 mOsm/kg. Alternatively, silicon-based antifoams and defoamers or nonionic surfactants such as coblock polymers of ethylene oxide/propylene oxide monomers may be added to the medium during fermentation. An example of a suitable commercial Serum-Free medium is EX-CELL® 293 Serum-Free Medium from Sigma-Aldrich. In special cases the medium may also be water. For microbial systems pH could be from 3 to 8 and temperature from 20 to 45 C. The skilled person knows how to find the right growth conditions for the chosen cell or microorganism.

The skilled person knows numerous suitable expression cells. In a preferred embodiment, the cell expressing the biopolymer (e.g. polypeptide) of interest is at least one cell selected from the group consisting of *E. coli, Bacillus*, yeast from the genus of *Saccharomyces, Pichia, Aspergillus, Fusarium, Kluyveromyces*, CHO (Chinese Hamster Ovary) cell, hybridomas, BHK (Baby Hamster Kidney) cell, myeloma cell, HEK-293 cell, human lymphoblastoid cell and a mouse cell, for example a NSO cell.

As used herein impurities are understood as chemical or biological compounds produced by the cells present in the bioreactor, which limit the growth of the cells. Impurities can also arise from cells that die or break open during the fermentation process. Impurities could comprise ethyl alcohol, butyl alcohol, lactic acid, acetone ethanol, gaseous compounds, peptides, lipids, ammonia, aromatic compounds and DNA and RNA fragments.

When the cells present in the bioreactor reaches a satisfactory cell density or when there is sufficient product present in the outflow through the harvesting outlet. This may be determined by measuring the cell density, by for example, using a spectrophotometer or measuring the amount of the polypeptide of interest by radioimmunoassay or other suitable protein assay methods. The skilled person knows how to measure the product of interest. The skilled person will know how to measure the presence of product of interest in the harvest stream.

Since the invention as described herein results in high cell density one may advantageously use the media with high cell density to re-start (e.g. seed) a new fermentation.

Cells that are advantageously subjected to the process of the invention may be any cell type benefiting from this process, i.e. culturing to a high viable cell density.

According to the process of the invention, a high viable cell density is preferably a density of at least 15 mill cells/ml, preferably at least 20 mill cells/ml, more preferably at least 25 mill cells/ml, even more preferably at least 30 mill cells/ml and most preferably at least 50 mill cells/ml.

In a suitable example the bioreactor containing one outlet having a separation device allowing impurities with a size below the size of the product, and medium to be removed while retaining the product in the bioreactor and outlet having a product harvest module allowing the product, impurities and medium to be removed may be regulated such that equal or different amounts of liquid may pass through the two outlets. This gives the possibility of concentrating the product of interest (e.g. polypeptide or cells) in the bioreactor as compared to a situation in where the bioreactor in operated without containing an outlet having a separation device allowing impurities to be removed while retaining the product in the bioreactor (as exemplified by working examples 1 and 2). In many cases it may be favourable to operate the bioreactor such that the outflow through the outlet having a separation device and the outflow through the outlet having a product harvest module are different. In one embodiment of the present invention the impurities are removed via the separation device by a flow rate of medium through the separation device that is at least 25%, such as at least 50%, e.g. such as at least 75% of the flow rate of medium through the product harvest module.

In a preferred embodiment of the present invention the impurities are removed via the separation device (e.g. the impurity filter unit) by a first flow rate through the separation device (e.g. impurity filter unit) and the product is harvested through the product harvest module by a second flow rate through the product harvest module, wherein the ratio between the first flow rate and the second flow rate is from 1:1 to 9:1.

In some cases it may be convenient to grow cells to a desired cell density in one bioreactor and then transfer the cells to a second bioreactor for inducing the expression of the polypeptide by adding an inducer or by changing the temperature and or the pH of medium. In such a case impurities may also be removed via the separation device of the first bioreactor by a desired flow rate and via the separation device of the second bioreactor by a the same or another desired flow rate.

In a preferred embodiment of the present invention impurities are removed via the separation device of the first bioreactor by a flow rate of medium through the separation device that is at least 25% of the flow rate of medium through the product harvest module of step (a of the fourth aspect), and wherein impurities are removed via the separation device of the second bioreactor by a flow rate of medium through the separation device that is at least 25% of the flow rate of medium through the product harvest module of step (b of the fourth aspect).

This is illustrated in working example 1 and 2 herein. In working example 1, the liquid outflow parameter is adjusted so that 4 L/hr is perfusing out through the product harvest module. In example 2, example 1 is repeated with the difference that the bioreactor is equipped with one outlet containing a separation device and a second outlet for harvesting the product. At day 10 when the cell density reaches 30 mill cells/ml the chemostat operation is initiated and the feed is split between harvest and waste. The optimized parameters is set to a feed rate of 7.5 L/day with 5 L/day perfusing out through the separation device and 2.5 liter perfusing out through the harvesting outlet and with a bioreactor temperature of 36.5° C. The HD chemostat is run for one week in this mode and results show is that the product concentration increases from 0.27 g/L to 1.38 g/L and the specific productivity increases from 0.27 g/L to 0.46 g/L per liter spend medium.

During the start of the fermentation when the level of product and impurities are low the separation device and the product harvest module may be closed such that no liquid pass through these units. When cell density increases and thereby also the levels of impurities, perfusion of liquid out through the separation device may be initiated as well as fresh medium may be supplied with the same rate to replenish consumed nutrients and expelled medium.

When the starting criteria for harvest is achieved, the outflow through the product harvest module is started and the system is readjusted such that fresh medium is feed with a rate corresponding to the sum of the outflow through the separation device and the product harvest module. In this way, outflow of impurities through the separation device may be adjusted according to the rate with which such impurities accumulate. In the same way, outflow of product through the product outlet may be adjusted according to the rate with which the product accumulates and consequently, fresh medium is feed with a rate corresponding to the sum of the outflow through the separation device and the product harvest module.

Accordingly, it might be beneficial to run the system with a lower outflow rate through the product harvest module than through the separation device such that the product is obtained in a more concentrated solution. In many cases this will facilitate further down stream processing and the cost involved.

Another advantage is for example, that unstable polypeptides which may be inactivated or degraded during prolonged time spent in the bioreactor may be harvested already at a low cell density through the product harvest module at low outflow rate while running the separation device at a high outflow rate. Similarly products, which are only expressed to low levels, can also be up-concentrated by the product harvest module such that the cost of the down stream purification can be optimized significantly. In addition, the chemostat culture may also be run at a lower growth rate and still keeping the productivity high since when operating the separation device a higher proportion of the cells is kept in the bioreactor.

In a number of situations one may advantageously add more new medium such as e.g. at least 1 time the bioreactor volume daily.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless other-wise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Example 1

A 5 L working volume chemostat is initiated according to the following: CHO cells expressing an IgG antibody at a specific productivity of 20 PCD (measured in a standard 10 day fed-batch) is inoculated into Ex-cell media. It is run as a fed-batch with feed of around 0.20 L/day for 7 days until it reaches a cell density of 12 mill cells/ml. Thereafter chemostat operation is initiated and the feed and bioreactor temperature is optimized to ensure constant cell density under chemostat operation. The optimized feed flow is set to 4 L/day and the cells are grown at 37.0° C. The chemostat is run for one week in this mode where after product concentration and productivity are measured.

Results show a product concentration of 0.27 g/L and productivity per bioreactor volume of 0.22 g/L day. The specific productivity is 18 PCD and productivity per liter spend medium is 0.27 g/L.

Example 2

Example 1 above is repeated in a bioreactor equipped with one outlet containing a separation device allowing impurities with a size below the size of the product, and medium to be removed while retaining the product in the bioreactor and a second outlet for harvesting the product. The bioreactor is operated for 5 days where after the separation device is activated and the fed-batch is continued to day 10 where it reaches a cell density of 30 mill cells/ml. Thereafter HD chemostat operation is initiated and the feed, is split between harvest and waste, and the bioreactor temperature was optimized to ensure constant cell density. The optimized parameters are determined to a feed rate of 7.5 L/day with 5 L/day discharged through the separation device and 2.5 L/day through the harvesting outlet and with a bioreactor temperature of 36.5° C. The HD chemostate is run for one week in this mode where after product concentration and productivity are measured.

Results show a product concentration of 1.38 g/L and productivity per bioreactor volume of 0.69 g/L day. The specific productivity is 23 PCD and productivity per liter spend medium is 0.46 g/L.

CONCLUSION OF RESULTS

Thus, by growing cells under standard chemostat conditions one may reach a product concentration of 0.27 g/L and productivity per bioreactor volume of 0.22 g/L day. However by splitting the chemostat feed into a in a waste fraction of 5 L/day that is passing through the separation device and a harvest fraction of 2.5 L/day that is passing through the harvesting outlet a much higher productivity and product concentration are obtained. Thus in this way one obtains a product concentration of 1.38 g/L and productivity per bioreactor volume of 0.69 g/L day compared to a product concentration of 0.27 g/L and productivity per bioreactor volume of 0.22 g/L day under standard chemostat conditions.

This is due to that the feed of fresh nutrients can be increased in a bioreactor having a separation device thereby reducing the amount of impurities and improving the relationship between cell growth and expression of the product. Moreover, as the outflow is separated into a product fraction containing cells and or product and a waste fraction containing impurities and spend media not allowing high value media components such as growth factors to leave the bioreactor it is possible to obtain improved productivity conditions with the opportunity to keep these valuable components in the tank for a prolonged time while still keeping level of impurities low and to control the flow of cells and product leaving the bioreactor. In addition, since fewer cells leave the bioreactor when the outflow is separated into a product fraction and a waste fraction the growth rate of the cells can be decreased either by lowering the temperature or regulating the gas (i.e., air, oxygen, nitrogen, carbon dioxide) flow rates, the dissolved oxygen levels or the agitation speed/circulation rate which may be beneficial for the stability or quality of the product.

It is also possible to keep a significant higher cell density and to obtain a more concentrated product in the harvest, while the productivity of the bioreactor show an increased productivity by a factor of 3 (0.69 g/L day compared to 0.22 g/L day), and the harvest concentration with a factor of 5 (1.38 g/L compared to 0.27 g/L). It is remarkable that this is achieved while at the same time the media consumption per gram of product being significantly reduced.

In conclusion, it is evident that the HD technology is a remarkable improvement to current chemostat technology.

REFERENCES

1: WO2011012725A1

The invention claimed is:

1. A method for producing a product selected from a biopolymer expressed by a cell, an intracellular or extracellular product produced by a cell or microorganism, a periplasmatic product produced by a cell or microorganism, a cell or a microorganism in a bioreactor in a chemostat fermentation process, wherein said bioreactor comprises:
   i) a first outlet having a separation device allowing impurities with a size below the size of the product, and medium to be removed while retaining the product in the bioreactor;
   (ii) a second outlet having a product harvest module allowing the product, cells, impurities and medium to be removed; and
   (iii) an inlet for adding a medium;
wherein the method comprises the following steps:
   (a) fermenting the cell expressing the biopolymer, the cell or microorganism producing the intracellular product, the cell, or microorganism producing the periplasmatic product, the cell, or the microorganism in the bioreactor in a suitable medium under suitable conditions, wherein during the fermentation impurities and medium are removed via the separation device, the product, cells, impurities and medium are removed via the product harvest module and new medium is added to replenish nutrients consumed by the cells or microorganisms and to equilibrate the medium removed during removal of impurities and harvesting the product; and
   (b) the product is isolated from the harvested medium; and
wherein the cell density in the bioreactor during the fermentation reaches at least 5 million cells per ml medium.

2. The method of claim 1, wherein the product is selected from a biopolymer.

3. The method of claim 1, wherein the product is selected from an intracellular product or from a periplasmatic product.

4. The method of claim 1, wherein the product is selected 5 from a microorganism or from a cell.

5. The method of claim 1, wherein the cell density in the bioreactor during the fermentation reaches at least 10 million cells per ml medium.

6. The method of claim 1, wherein impurities are removed via the separation device by one flow rate through the separation device and the product is harvested through the product harvest module by a second flow rate through the product harvest module, wherein the first flow rate refers to the flow rate of medium and impurities through the separation device and the second flow rate refers to the flow rate of product, cells, impurities and medium through the product harvest module, wherein the ratio between the first flow rate and the second flow rate is from 1:1 to 9:1.

7. The method of claim 1, wherein the separation device is selected from an impurity filter unit or a gravitational separation unit or a centrifugal separation unit.

8. The method of claim 1, wherein the bioreactor has a volume of at least 50 L.

9. The method of claim 1, wherein the separation device is a membrane filter having a nominal molecular weight cut-off (NMWC) pore sizes of at least 1000 NMWC.

10. The method of claim 1, wherein the separation device is a membrane filter having a nominal molecular weight cut-off (NMWC) pore size of a maximum of 80% of the MW of the product.

11. The method of claim 2, wherein the polypeptide is an antibody or fragment thereof, Human growth hormone, Follicle-stimulating hormone, Factor VIII, Factor VII, Factor IX Erythropoietin (EPO), Granulocyte colony-stimulating factor (G-CSF), alpha-glactosidase A, alpha-L-iduronidase (rhIDU; laronidase), N-acetylgalactosamine-4-sulfatase (rhASB; galsulfase), DNAse, Tissue plasminogen activator (TPA), Glucocerebrosidase, Interferon (IF), Insulin, Insulin derivative, Insulin-like growth factor 1, Tenecteplase, antihemophilic factor, human coagulation factor, Etanercept, Trastuzumab, Infliximab, Basiliximab, Belimumab, Daclizumab, Adalimumab Abciximabor, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

12. The method of claim 1, wherein the cell expressing the polypeptide is at least one cell selected from the group consisting of *E. coli, Bacillus*, yeast from the genus of *Saccharomyces, Pichia, Aspergillus, Fusarium, Kluyveromyces*, CHO (Chinese Hamster Ovary) cell, hybridomas, BHK (Baby Hamster Kidney) cell, myeloma cell, HEK-293 cell, human lymphoblastoid cell, a human cell and a mouse cell.

13. The method of claim 1, wherein the isolated polypeptide is formulated into a pharmaceutical composition.

14. The method of claim 2, wherein the biopolymer is a polypeptide or protein.

15. The method of claim 3, wherein the intracellular product is an inclusion body; wherein the periplasmatic product is a precipitated product in solid form; wherein the precipitated product in solid form is in crystalline, amorphous or denatured form.

16. The method of claim 4, wherein the microorganism is yeast or bacteria; wherein the cell is a mammalian cell.

17. The method of claim 6, wherein the separation device is an impurity filter unit.

18. The method of claim 7, wherein the separation device is a membrane filter, a gravitational separation unit or a centrifugal separation unit.

19. The method of claim 9, wherein the membrane filter has a nominal molecular weight cut-off (NMWC) pore sizes within the range of 2,000 to 15,000 NMWC.

20. The method of claim 12, wherein the human cell is a human cell.

* * * * *